United States Patent [19]

Kuraoka et al.

[11] 4,405,243
[45] Sep. 20, 1983

[54] CRYOGENIC IMPACT TESTING METHOD AND MACHINE

[75] Inventors: Yasuo Kuraoka; Norihide Hosoda, both of Sapporo, Japan

[73] Assignee: Hoxan Corporation, Sapporo, Japan

[21] Appl. No.: 334,320

[22] Filed: Dec. 21, 1981

[30] Foreign Application Priority Data

Dec. 26, 1980 [JP] Japan ............................. 55-189139
Oct. 6, 1981 [JP] Japan ......................... 56-148441[U]

[51] Int. Cl.³ .............................................. G01N 3/30
[52] U.S. Cl. ........................................ 374/46; 73/844; 73/12
[58] Field of Search .................... 73/12, 844; 374/45, 374/46, 51, 52

[56] References Cited

U.S. PATENT DOCUMENTS

| | | | |
|---|---|---|---|
| 2,404,584 | 7/1946 | Liska et al. | 374/52 |
| 2,450,880 | 10/1948 | Chatten et al. | 73/844 X |
| 2,491,512 | 12/1949 | Moore | 73/844 X |
| 2,579,424 | 12/1951 | Gehman | 374/46 |
| 2,670,624 | 3/1954 | Faris, Jr. et al. | 374/52 |
| 3,333,461 | 8/1967 | Gordon et al. | 374/46 |

OTHER PUBLICATIONS

An Apparatus for Metallographic Studies Between 4.2°°and 300 K. by M. V. Zinovier, L. K. Kolyboeu, Cryogenics, Apr. 1972, p. 134, vol. 12.
Apparatus for Thermal Cycling of Test Pieces Under Load; by I. Gindin, S. Krauchentco; Strength of Materials, Apr. 1973; No. 4, pp. 122-124; vol. 5.
Apparatus for Fatigue Tests in Vacuum at Low Temps.; by V. Bachmann in Rev. of Scientific Intr., vol. 45, No. 5, May 1974, pp. 702-704.
Apparatus for Impact-Fatigue Testing, by R. E. Schramm et al., Journal of Res. of Nat. Bur. of Stands., vol. 75C, No. 2, Apr.-Jun. 1971, pp. 95-98.

Primary Examiner—Stephen A. Kreitman
Assistant Examiner—David V. Carlson
Attorney, Agent, or Firm—George B. Oujevolk

[57] ABSTRACT

A cryogenic impact testing method of Charpy's and falling weight types which can test a test piece without substantially exposing the test piece with the atmospheric air under the same test piece cooling space, temperature controlling space and impact testing space, and a cryogenic impact testing machine of Charpy's and falling weight types which can execute suitably the above method. Thus, the stable temperature of the test piece can be obtained at the time of testing with highly reliable measured result.

4 Claims, 10 Drawing Figures

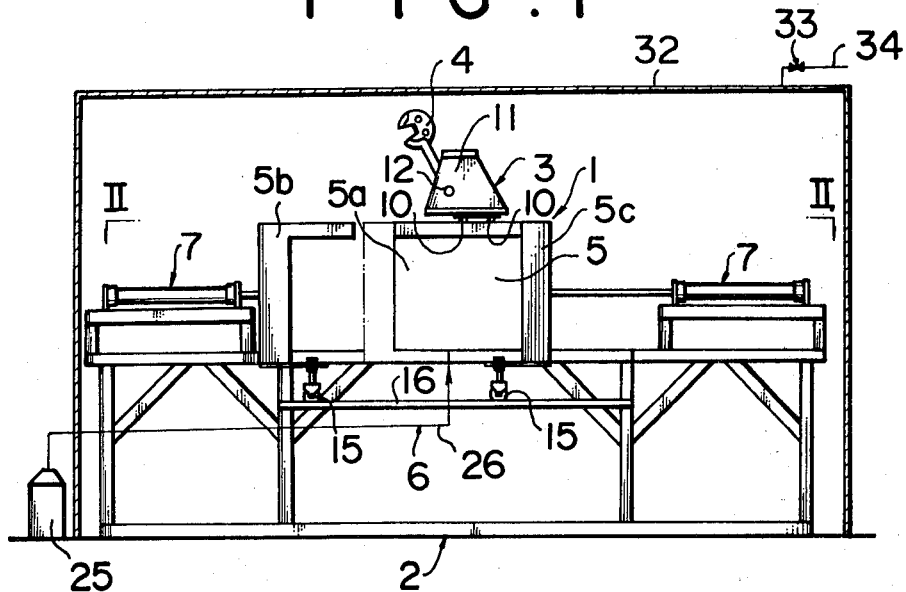
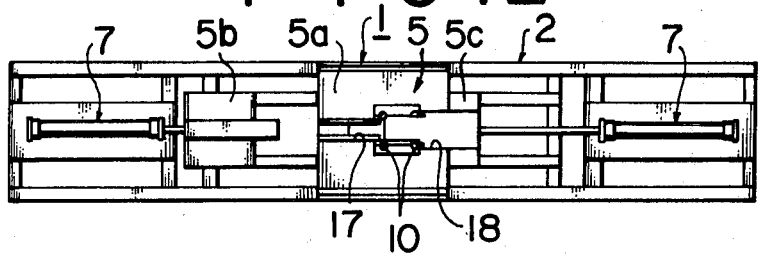
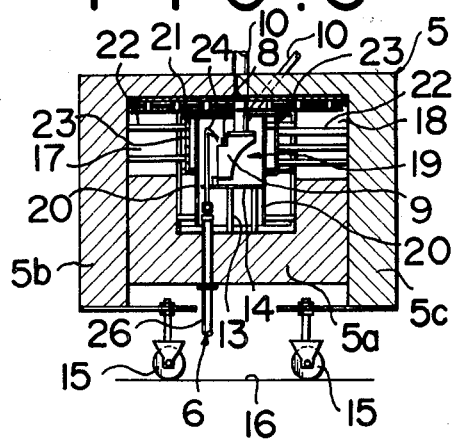
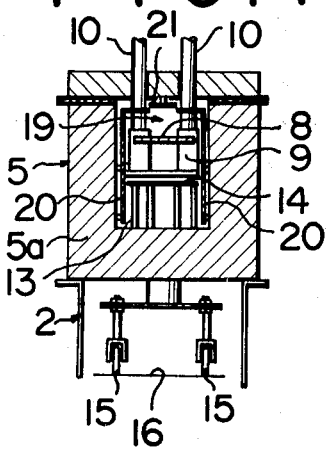

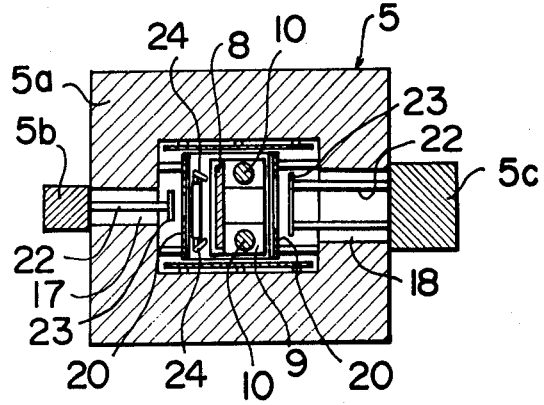
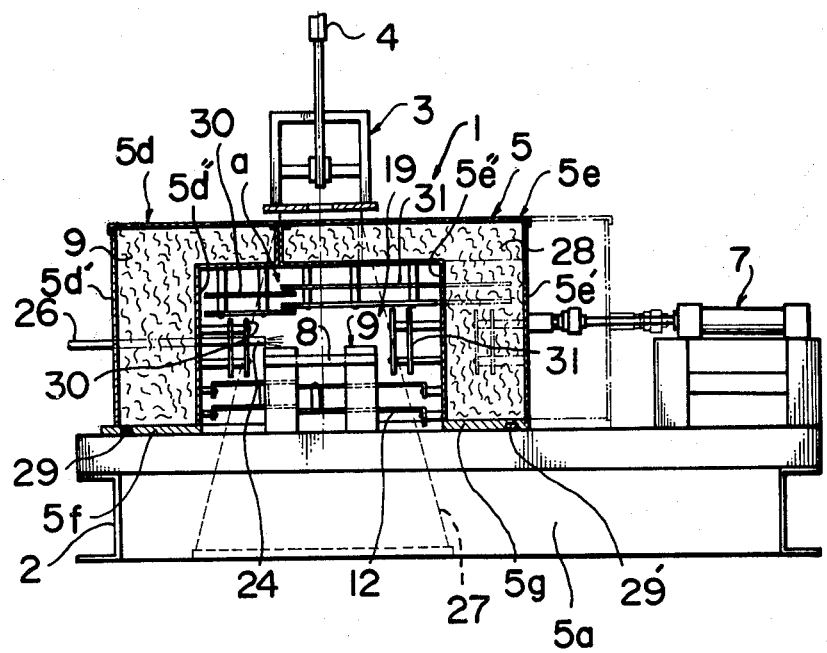

CRYOGENIC IMPACT TESTING METHOD AND MACHINE

BACKGROUND OF THE INVENTION

This invention relates to Charpy's or falling weight impact test for measuring the toughness of a test material at a cryogenic temperature and, more particularly, to a Charpy's or falling weight impact testing method for measuring the toughness of a test material at a cryogenic temperature and a testing machine for executing the method.

There are heretofore known as conventional testing method of the aforementioned type an impact testing method for testing the toughness of a test material at a cryogenic temperature having the steps of immersing the test material in a liquefied gas (such as, for example, alcohol, Freon or the like) cooled and retained at a low temperature, maintaining it for a predetermined time, rapidly moving the test material from the liquefied gas, setting the material in a testing machine and testing it; and an impact testing method for testing the toughness of a test material at a cryogenic temperature having the steps of enclosing the test material with a heat insulating material such as, for example, a foamed styrol, paper or the like formed in a box, setting the box in a testing machine, filling low temperature liquefied gas such as, for example, liquefied helium or the like therein, and testing the material in this state.

The specific heat of a substance generally becomes low at a low temperature, and when the temperature falls at a temperature particularly to that of liquefied gas, the specific heat of the substance becomes extremely low.

When a test material or piece of aluminum alloy is, for example, removed from liquefied helium to the air, it is reported that it is raised at temperature of 60° C. for 1.5 to 2 seconds according to its observation.

The former testing method of the above described ones has such disadvantages that, since the test material is exposed with the air after it is cooled, its temperature instantaneously rises and becomes unstable to cause the test at the set low temperature to become difficult and to also cause the measured value to lack its reliability.

On the other hand, the latter testing method of the above described ones has such disadvantages that, though it can eliminate the aforementioned disadvantages because the test material may not be exposed with the air, since the heat insulating box is destroyed at every test, it is not only inefficient but also troublesome and complicated because it must correct the effect of the heat insulating box to the measured value of the strength and it is difficult to control an arbitrary temperature in the method.

SUMMARY OF THE INVENTION

Accordingly, a primary object of this invention is to provide novel cryogenic impact testing method and machine in which all the aforementioned disadvantages and drawbacks of the conventional cryogenic impact testing method and machine are overcome.

Another object of this invention is to provide a cryogenic impact testing method of Charpy's and falling weight types which enables the testing of a test piece without substantially exposing the test piece with the air under the same test piece cooling space, temperature controlling space and impact testing space so as to thereby obtain stable temperature and highly reliably measured value.

A further object of this invention is to provide a cryogenic impact testing method of Charpy's and falling weight types which is not necessary to correct the effect of the heat insulating box to the measured value different from the conventional testing method necessary to destroy the heat insulating box at every test so as to obtain simple and highly reliably measured result.

Yet another object of this invention is to provide a cryogenic impact testing machine of Charpy's and falling weight types which can avoid the steps of removing the test piece into the atmospheric air and correcting the measured value with complicated work so as to improve the working efficiency of the impact testing.

Still another object of this invention is to provide a cryogenic impact testing machine of Charpy's and falling weight types which has high cooling efficiency and enables to recover low temperature liquefied gas in a case and to reuse it.

Still another object of the invention is to privide a cryogenic impact testing machine of Charpy's and falling weight types which is not necessary to destroy a heat insulating box so as to be economic and safely.

The above and other relates objects and features of the invention will be apparent from a reading of the following description of the disclosure found in the accompanying drawings and the novelty thereof pointed out in the appended claims.

BRIEF DESCRIPTION OF THE DRAWINGS

FIG. 1 is a front view showing one preferred embodiment of a testing machine executing the cryogenic impact testing method of the present invention;

FIG. 2 is a plan view of the machine shown in FIG. 1;

FIG. 3 is an enlarged longitudinal sectional view of the heat insulating box in the testing machine;

FIG. 4 is an enlarged longitudinal side sectional view of the heat insulating box;

FIG. 5 is an enlarged lateral sectional view of the heat insulating box;

FIG. 6 is a front view partly cut out showing another preferred embodiment of the testing machine of this invention;

DESCRIPTION OF THE PREFERRED EMBODIMENTS

Figure 7:
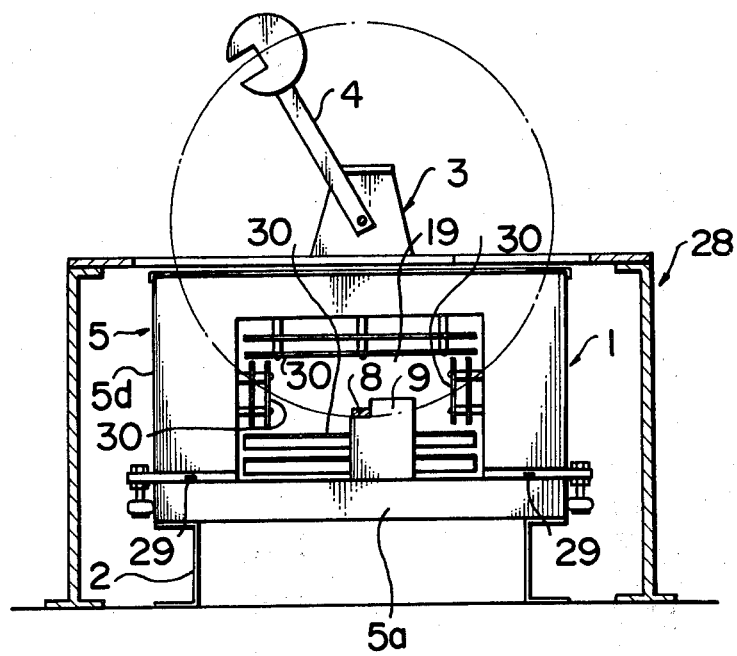
FIG. 7 is a longitudinal sectional side view of the testing machine shown in FIG. 6.

Reference is now made to drawings, particularly to FIGS. 1 and 2, which show a preferred embodiment of a cryogenic impact testing method constituted according to the present invention, wherein like reference numerals designate the same or equivalent parts and components in the following views.

In FIGS. 1 and 2, a testing machine 1 of the present invention comprises substantially at the center on a frame 2 constructed, for example, of L-shaped steel materials associated suitably laterally in a framework a hammer 4 or falling weight impact generator 3, a heat insulating box 5 placed on the frame, a low temperature liquefied gas supply unit 6, and driving means 7, 7.

It should be noted that though the embodiment shown employs the hammer 4 as impact generating means, it may also adopt a falling weight as described above.

The impact generator 3 comprises, as shown in FIGS. 3 through 5, a supporting base 9 for supporting a test piece 8, a plurality of main posts 10 stood on the base 9, the hammer 4 pivotally secured via a shaft 12 to the frame 11 thereof, the base 9 being placed above a shielding plate 14 fixed via studs 13 to the body 5a of the box 5 and thus fixed into the box 5 in such a manner that the generator 3 is projected upwardly from the box 5.

The heat insulating box 5 consists of the body 5a, and movable left and right parts 5b and 5c. The body 5a is fixed to the frame 2, while the movable parts 5b and 5c respectively have wheels 15 at the lower ends, which are engaged with rails 16 laid on the frame 2 so as to be laterally movable to enable to open and close the passages 17 and 18 of the hammer 4 so provided as to open at the upper right and left sides of the body 5a.

The passages 17 and 18 are so perforated as to be sufficient but minimum in size to pass the hammer 4. Shielding plates 23 are respectively provided inside via studs 22 together with shielding plates 14, 20, 21 provided within the body 5a for shielding low temperature testing space 19 having the base 9 in the body 5a at the movable parts 5b and 5c when the latter are closed.

The movable parts 5b and 5c are connected to driving means 7 such as a pneumatic cylinder or the like carried on the frame 2 to be laterally telescoped back and forth so as to open or close the passages 17 and 18.

The low temperature liquefied gas supply unit 6 comprises one or more of injection nozzles 24, 24 fixed to the body 5a of the box 5 for atomizing low temperature liquefied gas to the test piece 8, and a tube 26 so connected to the nozzles 24, 24 as to be thermally insulated in vacuum from a gas container 25 installed out of the testing machine.

The testing method and machine constructed according to the present invention as was composed will now be described.

When the movable parts 5b and 5c are solely (at the part 5b side in the exemplified embodiment) or together retarded by the driving means 7, 7 to open the passage 17 and the test piece 8 is set at the supporting base 9, the movable part 5b is moved to the side of the body 5a to close the passage 17.

Then, the liquefied helium or the like is atomized via the nozzles 24, 24 to the test piece 8 from the low temperature liquefied gas supply unit 6. After the test piece is thus cooled to a predetermined low temperature, the movable parts 5b, 5c are retarded by the driving means 7, 7, respectively to open the passages 17 and 18, and when the hammer 4 is simultaneously moved pivotally down to impact it to the test piece 8, the liquefied helium is continuously atomized to prevent the test piece 8 from rising at the temperature in such a manner that the test piece 8 may not be exposed with the atmospheric air even when the passages 17 and 18 are opened.

It should be noted that since the space for supporting the test piece 8 is the same as the impact testing space and the heat insulating box 5 enclosing the spaces is opened only at the part through which the hammer 4 passes as well as the liquefied helium or the like is atomized to the test piece 8 even after the passages 17 and 18 are opened, the temperature will now rise at the test piece and accordingly the impact test can be conducted at predetermined temperature.

It should also be noted that the operation of both the movable parts 5b and 5c for opening the passages 17 and 18 may be synchronized with the operation of pivotally moving down the hammer 4 with arbitrary means.

The excessive space in the heat insulating box 5 may contain a test piece to be tested in the next step. It should be noted that since the test piece can be precooled in this manner, it can shorten the time of cooling it to the set temperature when it is placed on the supporting base 9 in the testing.

Figure 8:
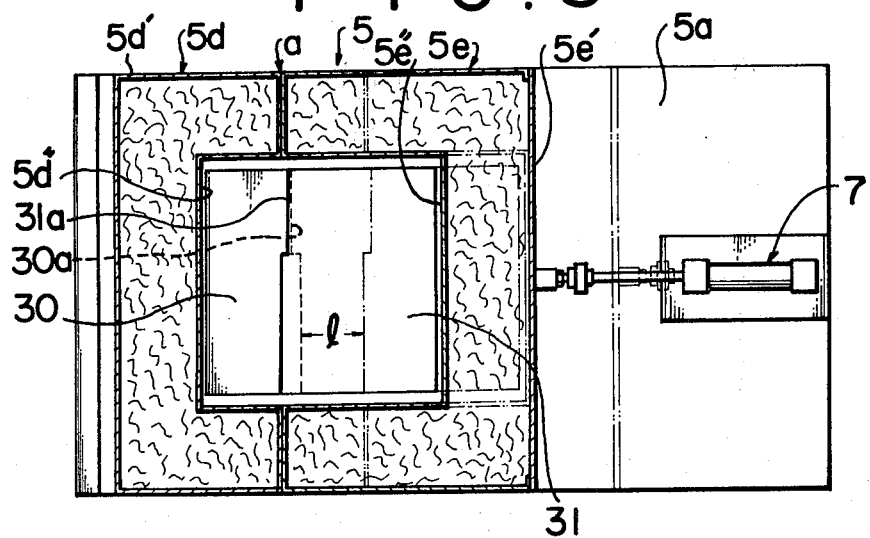
FIG. 8 is a plan view partly cut out of the testing machine shown in FIG. 6.

Another preferred embodiment of the impact testing machine will be described with reference to FIGS. 6 through 8. In FIGS. 6 through 8, in this testing machine 1 is provided a heat insulating box 5 which is constructed in a long body 5a placed on the frame 2 and which is so constructed as to form a low temperature testing space 19 enclosing the test piece 8 set on the supporting base 9 provided at the body 5a.

The heat insulating box 5 is different from that in the previous embodiment but consists of a stationary part 5d and a movable part 5e. The stationary part 5d is fixed onto the body 5a, while the movable part 5e is slidably placed on the body 5a, and they are connected to a predetermined driving means 17 such as a pneumatic cylinder or the like.

When the movable part 5e of the box 4 is opened, the hammer 4 is pivotally moved down synchronously therewith in the same manner as the previous embodiment. The impact generator 3 having the hammer 4 is mounted on another frame 27 different from the heat insulating box 5 fixed to the outside of the box 5.

The stationary and movable parts 5d and 5e forming the heat insulating box 5 are formed by surrounding heat insulating material 28 with outer and inner walls d', e' and d", e" made of stainless steel or the like as well as fixing sealing material 29 and sliding material 29' made of Teflon (trade name) difficult to cure at a low temperature to bottom plates f and g thereof so as to improve the sealing property thereof. The movable part 5e is formed slidably smoothly under the low temperature condition on the body 5a via the sliding material 29' made of Teflon (trade name).

It should be noted that the body 5a may be formed of reinforced plastic plate or the like.

Further, inside the stationary and movable parts 5d and 5e of the heat insulating box 5 are fixed preferably in double manner heat shielding plates 30 and 31 for enclosing the low temperature space 19. In the stationary part 5d one or more of injection nozzles 24 for atomizing low temperature liquefied gas to the testing space 19 are connected to a double wall heat insulating tube 26 insulated via vacuum from a gas container 25 in the same manner as the previous embodiment.

In the contacting part a between the stationary part 5d and the movable part 5e in the heat insulating box 5 the heat insulating plates 30 and 31 are so laterally laid as to partly superpose one another to prevent the introduction of cooling heat and heat from dissipating from the contacting part a and so formed in size as to be necessary and minimum to pass the hammer 4 at an interval 1 between the heat insulating plates 30 and 31 when the movable part 5e is slidably moved to open the movable part 5e for conducting the impact testing.

As shown in FIG. 8, cutouts 30a and 31a are formed at the rears of the heat shielding plates 30 and 31, respectively secured to the tops of the stationary and movable parts 5d and 5e, respectively so as not to destroy the plates due to the impact of the broken pieces of the test piece 8 after the hammer 4 is passed therethrough.

It should be appreciated that since the hammer 4 or the like is formed in this embodiment different from the heat insulating box 5 and mounted on the frame 27 fixed to the outside thereof, it does not dissipate the cooling heat from the hammer 4 nor introduce the outer atmospheric heat into the heat insulating box so as to improve the cooling efficiency and to enable the reduction in size of the driving means 7 in number of only one per one movable part 5e.

Still another preferred embodiment of the impact testing machine will be further described with reference to FIG. 1 in a different way.

The impact testing machine 1 of this embodiment is internally mounted in a case 32 made of transparent plate such as, for example, acrylic plate or the like so constructed as not to mix the low temperature liquefied gas with the atmospheric air even when the passages 17, 18 are opened to conduct the impact testing as was described above.

As shown in FIG. 1, a recovery tube 34 with a valve 33 is provided in the case 32 for recovering the low temperature liquefied gas for reuse when it is filled in the case 32.

Since the liquefied gas is not mixed with the air when the testing machine 1 is internally installed in the case 32 thus formed, it can completely prevent the temperature rise of the test piece 8. Since it can prevent the frost of the testing machine 1 and the heat insulating box 5 due to the mixture of the liquefied gas with the air, it can further improve the cooling efficiency of the test piece 8.

Still another preferred embodiment of the impact testing machine of this invention will be described with reference to FIGS. 9 and 10.

Figure 9:
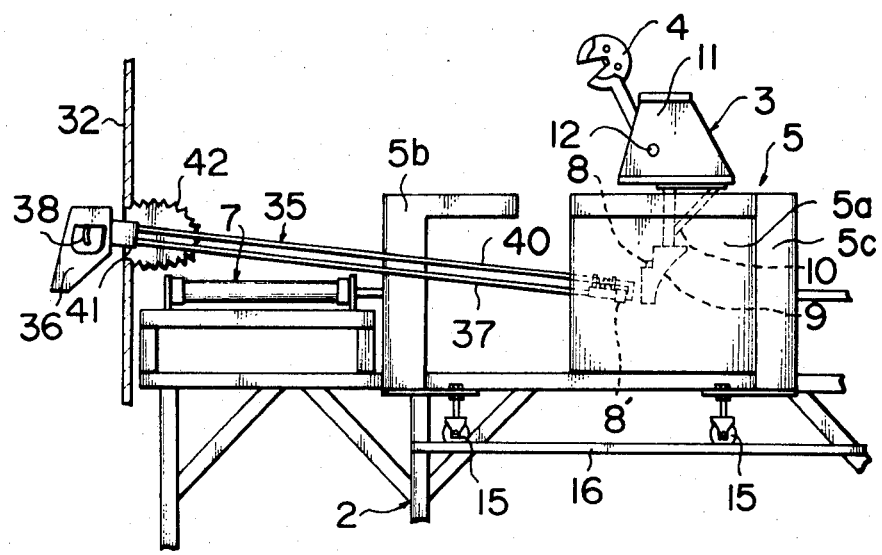
FIG. 9 is a partial front view showing the state that the magic hand is mounted at the testing machine.
Figure 10:
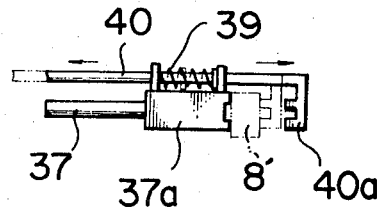
FIG. 10 is a partial side view showing one example of the magic hand.

In the testing machine 1 of this embodiment, in FIGS. 9 and 10, a magic hand 35 is so partly mounted partly in the case 32 as to be capable of carrying on the supporting base 9 from the outside of the case 32 airtightly.

The magic hand 35 has a supporting rod 37 with a grip 36 and a movable rod 40 slidably supported against the tension of a spring 39 by pulling a trigger 38 of the grip 36. When the trigger 38 is pulled, the rod 40 will slide against the tension of the spring 39. When the test piece 8' is interposed between the end of the rod 37 and the nipping pieces 37a and 40a provided at the end of the rod 40 and the trigger 38 is released, the rod 40 will slide toward the end via the spring 39 so as to release the test piece 8'.

It should be noted that the magic hand 35 may not be limited only to the construction described above but may also employ another construction formed arbitrary but in any case the case 32 is airtightly and movably supported via an O-ring or flexible bag 42 at the opening of the case 32.

It should be understood that since this embodiment of the impact testing machine can carry the precooled test piece 8' contained in advance in the excessive space of the testing space of the heat insulating box 5 on the supporting base 9 by way of the magic hand 35 in the sealed state of the testing machine 1, it can prevent the mixture of the air in the low temperature testing space 19 when the test piece is set and minimize the temperature rise of the test piece thus precooled conveniently.

It should be appreciated from the foregoing description that since in the cryogenic impact testing method according to the present invention the test piece 8 is set on the supporting base 9 and conducted in the impact testing within the space while cooling and controlling the temperature of the test piece, the test piece 8 may not be exposed with the atmospheric air and accordingly the test piece can be conducted in the impact testing stably at the temperature under predetermined low temperature condition, and since it is not necessary to correct the effect of the heat insulating box to the measured value different from the conventional testing method necessary to destroy the heat insulating box at every test, it can simply obtain highly reliable measured result.

It should also be understood that since in the cryogenic impact testing machine according to the present invention the heat insulating box 5 is so constructed as to open the passages 17 and 18 in size capable of passing the hammer 4 at the timing of dropping the hammer 4 to pass therethrough or the falling weight to pass therethrough, it can minimize the temperature rise of the test piece, and since the injection of the low temperature liquefied gas is continued even at the time of testing to eliminate the exposure of the test piece with the air, it can be applied suitably to the above described testing method and further since the testing machine 1 is installed in the case 32 and the magic hand 35 is mounted airtightly in the case 32, it can prevent the frost on the testing machine 1 and the heat insulating box 5 due to the mixture of the low temperature liquefied gas with the air with improved cooling efficiency, the liquefied gas can be recovered for reuse, and since the box 5 is not destroyed, it is economic and safely.

It should be noted that in order to maintain the test piece 8 at predetermined set temperature, a temperature detector is brought in contact with the test piece 8, and suitable means such as means for controlling the injection amount of the liquefied gas and the temperature of the liquefied gas by utilizing the output of the detector.

What is claimed is:

1. A cryogenic impact testing method of Charpy's and falling weight types comprising the steps of
    enclosing a testing space in a heat insulating box having an openable passage while a test piece is set on a supporting base,
    atomizing low temperature liquefied gas onto the test piece,
    opening the passage only sufficient for a hammer or a falling weight in the heat insulating box synchronously with the impacting operation of the hammer or the falling weight when the test piece reaches a set predetermined temperature, and
    conducting the impact testing of the test piece while continuing the atomizing of the low temperature liquefied gas even in the open state of the passage.

2. A cryogenic impact testing machine of Charpy's and falling weight types comprising:
    a test piece supporting base,
    hammer or falling weight impact generating means,
    a heat insulating box having a movable part for enclosing the low temperature testing space in the state that the test piece is set on the supporting base, and
    low temperature liquefied gas supplying means having an injection nozzle for atomizing the low temperature liquefied gas to the test piece in said heat insulating box, wherein said heat insulating box is mounted with predetermined driving means for opening the movable part thereof to provide a passage for said hammer or falling weight synchronously with the operation of said hammer or falling weight.

3. The testing machine according to claim 2, wherein said hammer or said falling weight is at least so internally mounted within a case as to prevent the mixture of the low temperature liquefied gas with the atmospheric air when the passage for said hammer or said falling weight is opened at the time of impact testing.

4. The testing machine according to claim 2, wherein said hammer or said falling weight is at least so internally mounted within a case as to prevent the mixture of the low temperature liquefied gas with the atmospheric air when the passage for said hammer or said falling weight is opened at the time of impact testing, and a magic hand capable of freely setting on said supporting base by the operation thereof from the outside of said case the test piece to be tested in the next step from the residual space of the low temperature testing space is airtightly mounted in said case.

* * * * *